US00RE42478E

(19) United States
(12) Reissued Patent
Kling et al.

(10) Patent Number: US RE42,478 E
(45) Date of Reissued Patent: Jun. 21, 2011

(54) METHOD OF MANUFACTURING A PANTS-TYPE DIAPER OF A SANITARY PANTY, AND ONE SUCH ABSORBENT ARTICLE

(75) Inventors: Robert Kling, Skene (SE); Urban Widlund, Pixbo (SE); Gunilla Hedlund, Ljungskile (SE)

(73) Assignee: SCA Hygiene Products Aktiebolag, Göteborg (SE)

( * ) Notice: This patent is subject to a terminal disclaimer.

(21) Appl. No.: 10/875,090

(22) PCT Filed: Apr. 11, 1995

(86) PCT No.: PCT/SE95/00390

§ 371 (c)(1),
(2), (4) Date: Oct. 4, 1996

(87) PCT Pub. No.: WO95/27461

PCT Pub. Date: Oct. 19, 1995

Related U.S. Patent Documents

Reissue of:
(64) Patent No.: 5,855,574
Issued: Jan. 5, 1999
Appl. No.: 08/714,105
Filed: Oct. 4, 1996

(30) Foreign Application Priority Data

Apr. 12, 1994 (SE) ..... 9401226-7

(51) Int. Cl.
*A61F 13/15* (2006.01)
*A61F 13/20* (2006.01)
*A61F 13/56* (2006.01)
*A41H 37/00* (2006.01)
*A44B 19/00* (2006.01)

(52) U.S. Cl. ..... 604/392; 604/386; 604/387; 604/393; 604/396; 156/66; 156/164; 156/204

(58) Field of Classification Search ..... 604/386–396; 156/66, 163–64, 204, 229
See application file for complete search history.

(56) References Cited

U.S. PATENT DOCUMENTS 1,458,082 A * 6/1923 Stein ..... 2/400
(Continued)

FOREIGN PATENT DOCUMENTS

AU 19998/83 9/1983
(Continued)

OTHER PUBLICATIONS

Translation of JP3-176051—21pgs.*
(Continued)

*Primary Examiner* — Michele Kidwell
(74) *Attorney, Agent, or Firm* — Buchanan Ingersoll & Rooney PC

(57) ABSTRACT

A method of manufacturing an absorbent article, and an absorbent article, in the form of a pants-type diaper or a sanitary panty, starting from a flat blank which includes an elongated absorbent body enclosed between two casing sheets which at opposing front and rear end parts of the absorbent body have side parts which extend laterally beyond the body on both sides thereof. The method includes the step of folding the blank around a transverse axis so that the end edges of the side parts lie edge-to-edge. At least one folded band of flexible material is placed between each pair of front and rear side parts which lie opposite one another in the folded state of the blank, and the free ends of the bands are fastened to adjacent side parts.

22 Claims, 2 Drawing Sheets

(Amended)

U.S. PATENT DOCUMENTS

| | | | | | |
|---|---|---|---|---|---|
| 1,494,044 | A | | 5/1924 | Ward et al. | |
| 1,833,960 | A | * | 12/1931 | Alsop | 604/394 |
| 1,998,140 | A | * | 4/1935 | Loew | 2/403 |
| 2,013,436 | A | * | 9/1935 | Downing | 604/398 |
| 2,085,425 | A | * | 6/1937 | Goodwin | 2/406 |
| 2,088,800 | A | * | 8/1937 | Malouf | 2/406 |
| 2,101,453 | A | * | 12/1937 | Rhodes | 604/392 |
| 2,119,610 | A | * | 6/1938 | Tasker | 604/401 |
| 2,122,873 | A | * | 7/1938 | Shuster | 2/126 |
| 2,141,105 | A | * | 12/1938 | Eller et al. | 604/394 |
| 2,165,561 | A | * | 7/1939 | Marcus | 604/397 |
| 2,179,675 | A | * | 11/1939 | Trageser | 2/93 |
| RE21,624 | E | * | 11/1940 | Dann | 2/406 |
| 2,257,426 | A | * | 9/1941 | Neiman | 2/80 |
| 2,272,830 | A | * | 2/1942 | Brody et al. | 2/406 |
| 2,366,031 | A | * | 12/1944 | James | 2/236 |
| 2,408,723 | A | * | 10/1946 | Arpin et al. | 2/403 |
| 2,411,129 | A | * | 11/1946 | Aprile | 2/402 |
| 2,419,867 | A | * | 4/1947 | Woodman | 2/403 |
| 2,452,129 | A | * | 10/1948 | Kaldor | 604/394 |
| 2,463,309 | A | * | 3/1949 | Prince | 2/67 |
| 2,471,048 | A | * | 5/1949 | Terchick | 604/386 |
| 2,477,914 | A | * | 8/1949 | Webb | 604/386 |
| 2,525,170 | A | * | 10/1950 | Ehrlich | 2/402 |
| 2,574,861 | A | * | 11/1951 | Cooley | 2/407 |
| 2,596,127 | A | | 5/1952 | Carmean | |
| 2,675,805 | A | | 4/1954 | Trimble | |
| 2,680,087 | A | * | 6/1954 | Sundback | 156/66 |
| 2,798,489 | A | * | 7/1957 | Behrman | 604/399 |
| 2,944,550 | A | | 1/1960 | Magid | |
| 3,187,343 | A | * | 6/1965 | Sage | 2/80 |
| 3,196,511 | A | * | 7/1965 | Kintner | 24/450 |
| 3,235,883 | A | | 2/1966 | Salamon | |
| 3,452,753 | A | * | 7/1969 | Sanford | 604/401 |
| 3,566,870 | A | * | 3/1971 | Benjamin | 604/399 |
| 3,605,665 | A | * | 9/1971 | Donald | 112/475.16 |
| 3,611,440 | A | * | 10/1971 | Zamist | 2/80 |
| 3,642,001 | A | * | 2/1972 | Sabee | 604/390 |
| 3,771,524 | A | * | 11/1973 | Ralph | 604/398 |
| 3,772,120 | A | * | 11/1973 | Radzins | 156/264 |
| 3,800,330 | A | * | 4/1974 | Bowcut | 2/227 |
| 3,823,445 | A | * | 7/1974 | Rivers | 24/432 |
| 3,828,785 | A | | 8/1974 | Gamm et al. | |
| 3,866,275 | A | | 2/1975 | Van Amburg | |
| 3,874,386 | A | | 4/1975 | Kozak | |
| 3,883,381 | A | | 5/1975 | Thaeler | |
| 3,901,239 | A | | 8/1975 | Tritsch | |
| 4,137,859 | A | * | 2/1979 | Itoh | 112/475.09 |
| 4,145,763 | A | | 3/1979 | Abrams et al. | |
| 4,186,744 | A | * | 2/1980 | Ness | 604/390 |
| 4,205,679 | A | * | 6/1980 | Repke et al. | 604/366 |
| 4,244,368 | A | | 1/1981 | Caradonna | |
| 4,259,957 | A | * | 4/1981 | Sonenstein et al. | 604/391 |
| 4,315,508 | A | * | 2/1982 | Bolick | 604/371 |
| 4,345,597 | A | * | 8/1982 | Tritsch | 604/390 |
| 4,404,243 | A | * | 9/1983 | Terpay | 428/62 |
| 4,523,333 | A | * | 6/1985 | Spangler | 2/49.3 |
| 4,555,244 | A | | 11/1985 | Buell | |
| 4,581,772 | A | * | 4/1986 | Smith | 2/111 |
| 4,610,680 | A | | 9/1986 | LaFleur | |
| 4,610,681 | A | | 9/1986 | Strohbeen et al. | |
| 4,617,022 | A | | 10/1986 | Pigneul et al. | |
| 4,638,509 | A | * | 1/1987 | Charron | 2/2.15 |
| 4,641,381 | A | * | 2/1987 | Heran et al. | 2/400 |
| 4,670,012 | A | * | 6/1987 | Johnson | 604/390 |
| 4,698,855 | A | | 10/1987 | Hicks | |
| 4,699,621 | A | * | 10/1987 | Stevens et al. | 604/385.29 |
| 4,699,622 | A | | 10/1987 | Toussant et al. | |
| 4,701,176 | A | | 10/1987 | Wilson et al. | |
| 4,726,807 | A | | 2/1988 | Young et al. | |
| 4,735,622 | A | | 4/1988 | Acuff et al. | |
| 4,739,910 | A | | 4/1988 | Westphal et al. | |
| 4,743,239 | A | | 5/1988 | Cole | |
| 4,747,846 | A | * | 5/1988 | Boland et al. | 604/385.22 |
| 4,771,483 | A | * | 9/1988 | Hooreman et al. | 2/237 |
| 4,834,738 | A | | 5/1989 | Kielpikowski et al. | |
| 4,834,820 | A | * | 5/1989 | Kondo et al. | 156/73.3 |
| 4,895,569 | A | | 1/1990 | Wilson et al. | |
| 4,909,804 | A | | 3/1990 | Douglas | |
| 4,920,575 | A | * | 5/1990 | Bartasis et al. | 2/457 |
| 4,938,757 | A | * | 7/1990 | Van Gompel et al. | 604/396 |
| 4,972,525 | A | * | 11/1990 | Hwang | 2/406 |
| 4,993,077 | A | * | 2/1991 | Robison | 2/82 |
| 5,019,073 | A | | 5/1991 | Roessler et al. | |
| 5,053,028 | A | * | 10/1991 | Zoia et al. | 604/385.21 |
| 5,064,421 | A | | 11/1991 | Tracy | |
| 5,074,854 | A | | 12/1991 | Davis | |
| 5,085,655 | A | | 2/1992 | Mann | |
| 5,085,658 | A | | 2/1992 | Meyer | |
| 5,087,253 | A | | 2/1992 | Cooper | |
| 5,147,487 | A | | 9/1992 | Nomura et al. | |
| 5,170,505 | A | * | 12/1992 | Rohrer | 2/69 |
| 5,176,671 | A | | 1/1993 | Roessler et al. | |
| 5,196,000 | A | | 3/1993 | Clear et al. | |
| 5,204,997 | A | * | 4/1993 | Suzuki et al. | 2/400 |
| 5,213,645 | A | | 5/1993 | Nomura et al. | |
| 5,269,776 | A | | 12/1993 | Lancaster et al. | |
| 5,324,279 | A | | 6/1994 | Lancaster et al. | |
| 5,340,424 | A | | 8/1994 | Matsushita | |
| 5,366,453 | A | | 11/1994 | Zehner et al. | |
| 5,370,634 | A | | 12/1994 | Ando et al. | |
| 5,374,262 | A | * | 12/1994 | Keuhn et al. | 604/391 |
| 5,386,595 | A | * | 2/1995 | Kuen et al. | 2/400 |
| 5,411,498 | A | * | 5/1995 | Fahrenkrug et al. | 604/385.22 |
| 5,462,540 | A | * | 10/1995 | Caldwell | 604/389 |
| 5,531,732 | A | | 7/1996 | Wood | |
| 5,591,155 | A | * | 1/1997 | Nishikawa et al. | 604/393 |
| 5,607,537 | A | | 3/1997 | Johnson et al. | |
| 5,628,738 | A | | 5/1997 | Suekane | |
| H1674 | H | | 8/1997 | Ames et al. | |
| 5,662,638 | A | | 9/1997 | Johnson et al. | |
| 5,779,831 | A | * | 7/1998 | Schmitz | 156/73.1 |
| 5,830,206 | A | | 11/1998 | Larsson | |
| 5,855,574 | A | | 1/1999 | Kling et al. | |
| 6,042,673 | A | | 3/2000 | Johnson et al. | |
| 6,210,388 | B1 | | 4/2001 | Widlund et al. | |
| 6,328,725 | B2 | * | 12/2001 | Fernfors | 604/391 |
| 6,395,115 | B1 | * | 5/2002 | Popp et al. | 156/66 |
| 6,409,858 | B1 | * | 6/2002 | Popp et al. | 156/66 |
| 6,432,243 | B1 | * | 8/2002 | Popp et al. | 156/204 |
| 6,461,344 | B1 | | 10/2002 | Widlund et al. | |
| 2003/0135190 | A1 | | 7/2003 | Widlunc et al. | |

FOREIGN PATENT DOCUMENTS

| | | | | |
|---|---|---|---|---|
| CO | 296601 | | | 7/1989 |
| EP | 0187728 | A2 | | 7/1986 |
| EP | 0 320 991 | A2 | | 6/1989 |
| EP | 0320989 | B1 | | 6/1989 |
| EP | 0417766 | | | 4/1994 |
| FR | 2331975 | A | * | 7/1977 |
| FR | 2624353 | A1 | * | 6/1989 |
| GB | 947346 | | | 1/1964 |
| GB | 1356465 | | | 6/1974 |
| GB | 2035053 | A | * | 6/1980 |
| GB | 2107172 | | | 4/1983 |
| GB | 2129689 | | | 5/1984 |
| GB | 2 130 888 | | | 6/1984 |
| GB | 2 130 888 | A | | 6/1984 |
| GB | 2 144 637 | | | 3/1985 |
| GB | 2244422 | | | 12/1991 |
| GB | 2245149 | | | 1/1992 |
| GB | 2267024 | | | 11/1993 |
| GB | 2 144 637 | A | | 3/1995 |
| JP | 63-243307 | | | 10/1988 |
| JP | 3-176051 | | | 7/1991 |
| JP | 03195555 | A | * | 8/1991 |
| JP | 03-268756 | | | 11/1991 |
| JP | 4-000828 | | | 1/1992 |
| JP | 4-28363 | | | 1/1992 |
| JP | 04144558 | A | * | 5/1992 |
| JP | 4-161152 | | | 6/1992 |
| JP | 5-009530 | | | 2/1993 |
| JP | 5-293135 | | | 11/1993 |
| JP | 07-080023 | | | 3/1995 |
| PL | 170375 | | | 5/1993 |
| WO | WO93/17648 | | | 9/1993 |

| | | | |
|---|---|---|---|
| WO | WO 9324085 | A1 * | 12/1993 |
| WO | 94/01070 | | 1/1994 |
| WO | WO 95/27461 | | 10/1995 |

OTHER PUBLICATIONS

Definitions of "a", "tape", "fabric" and "cloth", Merriam-Webster OnLine.*

Notice of Opposition issued in corresponding European Patent No. 0755237 B1.

Interlocutory Decision issued in Opposition proceedings in corresponding application No. EP 0 755 273, dated Nov. 18, 2009.

Minutes of the Oral Proceedings before the Opposition Division issued in corresponding application No. EP 0 755 273, dated Nov. 18, 2009.

* cited by examiner

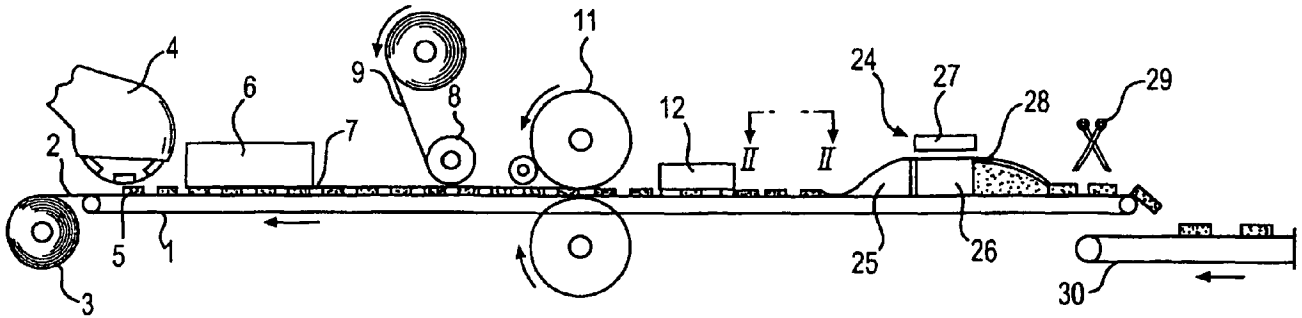
FIG. 1
(Amended)
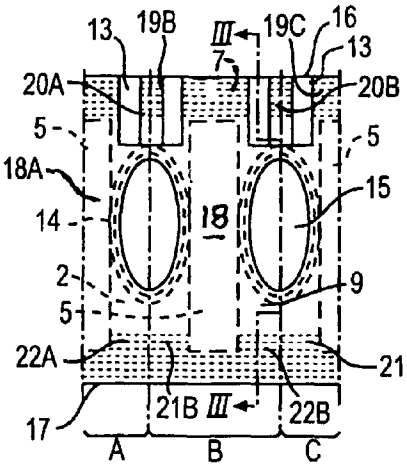
FIG. 2
(Amended)
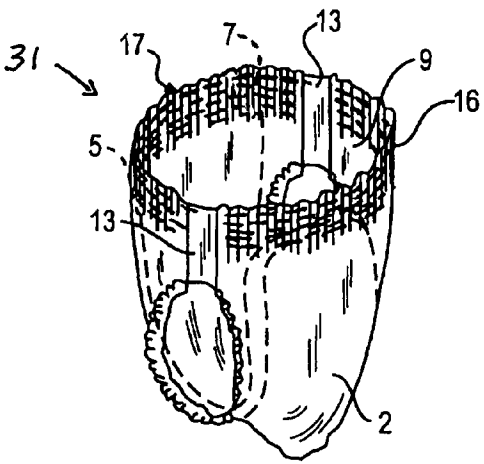
FIG. 4
(Amended)

METHOD OF MANUFACTURING A PANTS-TYPE DIAPER OF A SANITARY PANTY, AND ONE SUCH ABSORBENT ARTICLE

Matter enclosed in heavy brackets [ ] appears in the original patent but forms no part of this reissue specification; matter printed in italics indicates the additions made by reissue.

TECHNICAL FIELD

The present invention relates to a method of manufacturing an absorbent article in the form of a pants-type diaper or a sanitary panty, beginning with a flat diaper blank which comprises an elongated absorbent body enclosed between two casing sheets which at opposing front and rear end parts of the absorbent body have side parts which extend laterally beyond the absorbent body on both sides thereof, said method comprising the step of folding the blank about a transverse axis so that the end edges of said side parts will lie edge-to-edge. The invention also relates to an absorbent article manufactured in accordance with the method.

BACKGROUND OF THE INVENTION

Present-day all-in-one diapers are being replaced to an ever greater extent with pants-type diapers, or so-called training pants, for slightly older diaper-wearing children. Pants-type diapers have a number of good features. They fit well on the wearer, they are easy to put on and take off with the child in a standing position, they sit firmly in place after having been put onto a child, and conform to the anatomy of the child as the child moves, in a comfortable fashion. Moreover, pants-type diapers resemble conventional underpants and it is easy to understand how they shall be used, thereby in many instances enabling somewhat older diaper-wearing children to perform themselves the simple operations required in putting on the pant diaper.

EP A2-0,320,991 defines a pants-type diaper which is produced by folding a blank of the aforesaid kind in the manner described in the introduction, whereafter the bordering side edges of the side parts are fastened together by ultrasonic welding or gluing. A pants-type diaper manufactured in this way will necessarily have at least two outwardly standing side seams which, when the diaper is worn, are subjected to loads or forces that are directed generally at right angles to the bonded surfaces, i.e. to so-called peel forces. Consequently, the side seams must be sufficiently strong to withstand the forces to which they are subjected, meaning that a high degree of precision is required when joining the surfaces together and also when selecting the materials to be joined. Neither are the seams attractive from an aesthetic point of view, which is a negative feature from a commercial aspect.

SUMMARY OF THE INVENTION

An object of the present invention is to provide a pants-type diaper or a sanitary panty having side seams which from a loading aspect are more advantageous than side seams that are subjected to peeling forces, and which has aesthetically attractive side parts.

This object is achieved in accordance with the invention by means of a method of the kind defined in the introduction which is characterized by placing at least one folded band of flexible material between each pair of front and rear side parts that lie opposite one another in the folded state of the blank, and by fastening the free ends of the band to respective adjacent side parts.

According to one preferred embodiment of the invention, the folded bands are placed on and fastened to the front or rear side parts of the blank prior to folding said blank, and the band is folded in a bellows like fashion prior to fastening the same to the side parts.

This method can also be applied even when the blanks form a continuous string, i.e. prior to separating the individual blanks from said string.

When, for reasons of a production/technical nature, the blanks are separated individually from a continuous string of blanks prior to bringing the side parts together, it is proposed in accordance with the invention that a method of [tie] *the* kind defined in the introduction will include the characterizing steps of folding at least one band of flexible material around each pair of the front and rear side parts of the web which oppose one another in the folded state of said web, and by fastening the free ends of the band to its adjacent side part.

The invention also relates to an absorbent article in the form of a pants-type diaper or sanitary panty, which comprises an elongated absorbent body enclosed between two casing sheets which have at opposing front and rear end parts of the absorbent body side parts which extend laterally beyond said body on both sides thereof, wherein the opposing front and rear side parts are mutually joined, characterized in that a separate piece of material extends between each pair of mutually opposing front and rear side parts and forms a joint between these side parts such that said joint will be subjected essentially to shear forces when the article is worn.

According to one preferred embodiment of the invention, the pieces of material joining the side parts are generally non-elastic and the separate pieces of material are attached to the inner surfaces of the side parts. The separate pieces of material are comprised of two separate parts which are joined together by a releasable and refastenable fastener means, for instance in the form of a row of press studs, projections and recesses, mutually coacting hooks and eyes, adhesive coatings or self-fastening or hook and loop fasteners.

BRIEF DESCRIPTION OF THE FIGURES

The invention will now be described in more detail with reference to the accompanying drawings, in which FIG. 1 illustrates schematically a plant machinery for manufacturing a pants-type diaper in accordance with the invention and by means of an inventive method;

FIG. 2 illustrates from above a part of the web shown in FIG. 1 in a manufacturing stage immediately prior to folding and joining together the blanks to form pants-type diapers;

FIG. 4 is a perspective view of a pants-type diaper manufactured in accordance with the inventive method;

DETAILED DESCRIPTION OF THE PREFERRED EMBODIMENTS

Figure 3:
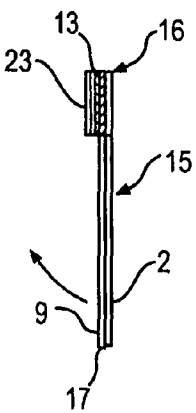
FIG. 3 is a sectional view taken on the line III-III in FIG. 2 *but with the elastic threads 7 in FIG. 2 omitted and glue beads 23 added*.

FIG. 1 illustrates schematically the plant machinery for manufacturing pants-type diapers, including a conveyor path 1 by means of which casing material 2 taken from a storage reel 3 is conveyed from left to right in FIG. 1. Located downstream of the reel 3 is a device 4 which lays absorbent bodies 5 at regular intervals on the underlying web of casing material 2. Located downstream of the device 4 is a device 6 which lays elastic elements in a specific pattern onto or immediately above the web of casing material 2. These elastic elements, of which one is shown schematically [in] by reference numeral 7 FIG. 1 and which are preferably comprised of elastic threads or ribbons, form the waist and leg elastic of the manufactured pants-type diaper. Located downstream of the device 6 are guide rollers 8 which function to guide a second web of casing material 9 onto the first web 2, while downstream of the guide rollers 8, there is located a device 11 which brings the webs of casing material together and fastens the webs to one another at those parts thereof which lie outside the absorbent bodies 5. The plant machinery hitherto described functions in the same way as the plant machinery used to manufacture conventional all-in-one diapers and the composite product leaving the device 11 will be comprised of a continuous string of pants-type diaper blanks which, similar to the all-in-one diapers produced in conventional plants, includes an absorbent body which is enclosed between two casing sheets and also elastic elements. At this stage of manufacture, the pants-type diaper blank differs from a typical diaper blank mainly in that the waist elastic has a different form as will be made more apparent in the following. The devices 4, 6, 8 and 11 are preferably known devices suitable for producing a pants-type diaper blank of the aforesaid kind. Since a detailed description of the construction of these devices is not needed to acquire an understanding of the invention, the devices will not be further described.

Located downstream of the device 11 is a device 12 which functions to attach folded bands 13 to the underlying moving web of mutually connected blanks. The device 12 will preferably include plungers that are operative in pressing glue-coated bands 13 against the casing sheet 9.

FIG. 2 illustrates from above a section of the web of mutually joined blanks subsequent to the web exiting from the device 12. The section illustrated in the Figure includes a complete pants-type diaper blank B and parts of two mutually adjacent blanks A and C. As will be seen from the Figure, the device 6 lays-out a plurality of elastic threads 7 which extend sequentially in the transverse direction of the blank and which form the waist elastic of a manufactured pants-type diaper. The device 6 also lays-out around openings 15 cut from the web elastic threads 14 which form the leg elastic of a manufactured pants-type diaper. The openings are preferably cut from the web when joining the casing sheets together with the aid of some appropriate means, for instance by means of a punch included in the device 11 or located immediately downstream thereof.

The blanks A, B, C include a front edge 16, a rear edge 17, a central part 18 delimited by the opposing long edges of the absorbent body 5 and the extensions of said long edges, front side parts 19, 20 on both sides of the central part 18, and rear side parts 21, 22 which are delimited by the respective front edge 16 and rear edge 17, the openings 15 lying on respective sides of the central part, and the imaginary separation lines between the individual blanks A, B and C, which are shown in dash-dotted lines in FIG. 2. When applicable, the parts 19-22 of the various diapers have been further identified in FIG. 2 with the aid of suffixes A-C, in order to clearly distinguish between corresponding parts of different blanks. As shown in FIG. 3, the bands 13 attached to the side parts 19, 20 are single-folded and are disposed with respective folds extending parallel with the side edges of the side parts, so that those edges of the band that are folded towards one another in said side parts will face one another.

Pants-type diapers are produced from the blanks shown in FIGS. 2 and 3, simply by folding the blanks in the direction indicated by the arrow in FIG. 3, so that the edges 16 and 17 will lie opposite one another, and by fastening the casing sheet 9 to the bands 13 in conjunction therewith. Glue beads 23 are suitably applied to the single-folded bands 13 in conjunction with bringing the edges 16, 17 together. Naturally, the glue beads may instead be applied to the casing sheet 9 on the rear side parts 21, 22 prior to folding the blanks.

The plant illustrated in FIG. 1 includes downstream of the device 11 a device 24 by means of which the web of blanks is folded together and the front and rear side parts of the blanks are joined to one another. The device 24 may include fixed guide means 25 having mutually successively converging side walls, plunger means 26 which intermittently press the rear side parts of the blanks against the front side parts thereof, applicator means 27 for applying glue to the folded bands or to the rear side parts, and fixed guide means 28 having side walls which successively diverge from one another.

The web moving through the guide means 28 is thus comprised of a string of mutually joined pants-type diapers which after exiting from the guide means 28 are separated from one another by means of an appropriate cutting tool 29 and conveyed by suitable conveying means 30 to a packaging station.

FIG. 4 is a perspective view of a pants-type diaper manufactured in accordance with the aforedescribed method. A pants-type diaper is intended to be put on in the same way as a pair of underpants and is characterized by an elasticated waist part which can be stretched so that the diaper can be drawn readily over the wearer's hips when putting on or taking off the pant diaper, and the elasticity of which is such that a worn pant diaper will be held securely in position by the contraction forces acting in the waist part of the diaper. In order to fulfil these functional requirements while, at the same time, restricting the number of production sizes, the pants-type diaper will preferably have a stretchability which is greater than 80%, i.e. the circumference of the waist part shall be 1.8 times the extension of the circumference of the waist part of a removed pant diaper in a non-stretched state. The total contraction force in the waist part, i.e. the sum of the force contributed by elastication provided in the front part, the rear part and the side parts, will preferably exceed 3N.

The pants-type diaper illustrated in FIG. 4 is constructed in the same way as the pants-type diaper described in Swedish Patent Application No. 9200663-4, and includes an absorbent body 5 enclosed between an inner and an outer casing sheet 9 and 2 respectively. The inner casing sheet 9 is liquid-permeable and is comprised, for instance, of non-woven material compiled from fibres of polyethylene, polypropylene, polyester or mixtures thereof. Viscose fibres may also be used. It is also conceivable to form the inner casing sheet from a perforated plastic sheet, for instance a perforated polyethylene sheet. The outer casing sheet 2 is liquid-impermeable or at least hydrophobic and may, for instance, comprise a sheet of polyethylene or nonwoven material which has been coated with or laminated with polyolefins, so as to be made liquid-impermeable or at least hydrophobic. For aesthetic and psychological reasons, the outer casing sheet 2 may be comprised of two layers, an inner liquid-impermeable layer and a layer of fabric-like material disposed outside the inner layer. The wearer will then see and feel the pant diaper as a fabric garment rather than as a plastic garment. When the outer casing sheet has this latter construction, it is not necessary for the liquid-impermeable sheet to have the same extension as the fabric-like sheet, but may be smaller than said sheet, for instance liquid-impermeable casing material can be omitted from the side parts of the pant diaper.

The absorbent body 5 may contain cellulose fluff pulp with or without an admixture of particles of so-called superabsorbent material and/or thermoplastic melt fibres, and may be comprised of one or more layers.

The waist part [41] *31* of the pants-type diaper illustrated in FIG. 4 includes a plurality of sequentially mounted elastic threads 7, each of which extends transversely around the circumference of the waist part. In this way, there is formed a relatively broad elastic waist part. As will be understood, elastic ribbons, bands or the like may be used instead of elastic threads, or other elastically stretchable material can be used, such as elastically stretchable plastic film, an elastically stretchable nonwoven material, or like material.

Similar to a pair of underpants, the pants-type diaper illustrated in FIG. 4 has a waist opening and two leg openings, which are provided with leg elastic in a conventional manner. The pant diaper is put on by inserting the legs of the wearer through the leg openings and then drawing the pant diaper up over the wearer's hips. The contraction forces exerted by the elastic elements at the waist opening, i.e. at the uppermost part of the waist part [41] *31*, are preferably greater than the contraction forces exerted in the remainder of the waist part. This will ensure that the pant diaper will remain seated in its intended position, even when the absorbent body is full of urine.

Thus, when the pants-type diaper is worn, the joint between the bands 13 and the casing sheet 9 will be affected essentially only by forces that act in the circumferential direction of the waist part, said joints therewith solely being subjected to shear forces. As a result of the construction of the inventive pant diaper, the joint will not be subjected to peeling forces that are unfavourable from a loading aspect. Consequently, the requirements placed on the properties of these joint are much less stringent than the requirements placed on the joint of known pants-type diapers. The joint produced by the inventive method are also attractive from an aesthetic aspect and fulfil the purpose of imitating conventional underpants in a much better manner than the earlier known pants-type diapers.

The inventive method also provides certain technical manufacturing advantages over the known method of joining together the side parts of a pants-type diaper taught by the aforesaid EP-A2-0,320,991. When manufacturing the known pants-type diaper, a greater degree of precision is required when joining the edges of the side parts together, both with regard to folding the blanks so that the side edges of the front and rear side parts will lie edge-to-edge, and with regard to the actual joining process, in which a welding or gluing unit must be guided with the same precision. When practicing the inventive method, it is immaterial from a functional aspect whether or not the bands are slightly displaced from their intended position on the front side parts when mounting the bands on the underlying web or string of blanks, or whether or not the glue beads 23 (FIG. 3) are slightly displaced laterally from their intended position subsequent to said application, provided of course that the bands are dimensioned to permit such deviations. The same advantages are, of course, obtained when other methods, such as ultrasonic or heat-sealing methods are used to fasten the bands and casing material together instead of glue. Because the joins are only subjected to shear forces, there is a greater freedom in the type of joint chosen, for instance the joint used may be a mechanical joint of a self-fastening type.

Figure 5:
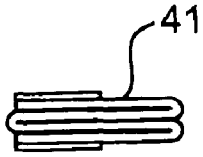
FIG. 5 illustrates a bellows-folded band suitable for application on an inventive pants-type diaper blank manufactured by means of the transverse production method, i.e. the absorbent bodies have been placed on a moving web of material with the longitudinal axes of the bodies extending at right angles to the direction of web movement.

Another advantage is that the circumferential extension of the bands 13 can be varied to a large extent, and if desired this extension can be made sufficiently large to enable the side parts of the diaper to be comprised almost completely of said bands. This construction will reduce the waste of casing material, since the lateral extension of the openings in the string or web of blanks will be reduced to a corresponding extent. However, in the case of this construction, it is not possible to attach the bands in a single-folded state to the pants-type diaper blank, since the bands would then be severed when cutting the individual blanks from the blank string. In order to enable bands of greater extension in the circumferential direction of the manufactured diaper to be applied, it is necessary to fold the bands in a bellows fashion prior to application, so as to restrict the extension of the bands in the transverse direction of the blanks. FIG. 5 illustrates an example of a bellows-folded band [31] *41* which can be applied to a pants-type diaper blank in the same way as the bands 13.

The aforedescribed method of mounting the bands on the side parts of a pants-type diaper blank can be applied in both transverse and longitudinal production of pants-type diapers, although with the difference that in the case of longitudinal production, it is necessary to cut the individual blanks from the blank string prior to folding the rear side parts onto the front side parts.

When the blanks are advanced in the form of individual blanks, the bands can be applied to the casing sheet 2 instead of to the casing sheet 9, by first fastening one free end of the bands to the front side parts of the blank, and thereafter folding the blank. The bands, which are initially not folded and flat, are then folded in over the rear side parts of the folded blank and fastened thereto. Naturally, it is also possible to apply the flat bands to the front side parts of the individual, flat blanks, whereafter the blank and then the bands are folded, wherewith the bands will be attached to the inner surfaces of the front side parts and the outer surfaces of the rear side parts.

In this regard, it is pointed out that the bands may, of course, be fastened to the front and the rear side parts in a reverse manner to that described, i.e. the bands may be first fastened to the rear side parts and then to the front side parts.

Figure 6:
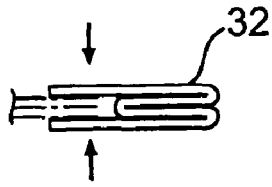
FIG. 6 illustrates a bellows-folded band suited for application on an inventive pants-type diaper blank *illustrated in broken lines and* manufactured in accordance with the longitudinal production method, i.e. the absorbent bodies have been placed on a moving web of material with the longitudinal axes of the bodies extending parallel with the direction of web movement.

FIG. 6 illustrates a band 32 which can be fastened to a ready folded blank, by passing the blank side parts that have been folded onto one another between the free edges of the band 32 and pressing these edges firmly onto the side parts, by application of an external force. *When the band 32 is unfolded, the joint lies in a plane which is the same plane as the opposing front and rear side parts in that outside surfaces of the front and rear side parts are attached to a same side of the band and the joint will be subjected essentially to shear forces when the article is worn.*

According to one variant of the method described with reference to FIGS. 1-4, the folded bands can be passed in between the front and the rear side parts during the final stage of folding the blanks and fastened thereto in one single stage.

As mentioned in the aforegoing, pants-type diapers have a number of good features, but also some drawbacks. It is difficult to change a pants-type diaper with the wearer in a lying position, and requires the removal of a garment worn outside the pant diaper when making the change. Neither can a used pants-type diaper be rolled up and sealed in the same way as an all-in-one diaper. Furthermore, the diaper wearer is liable to be dirtied when removing a used pant diaper containing feces.

Figure 7:
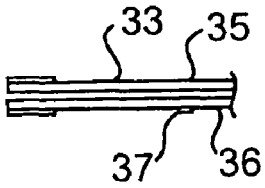
FIGS. 7 and 8 illustrate folded bands which include releasable and refastenable fastener means, suitable for application on an inventive pants-type diaper blank.
Figure 8:
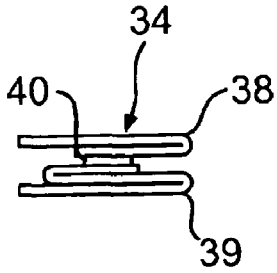
Figure 9:
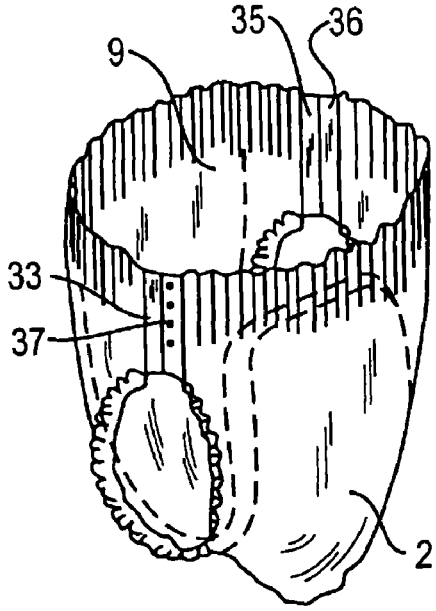
FIG. 9 illustrates in perspective a second embodiment of a pants-type diaper which includes the bands of FIG. 7 in its side parts.

These drawbacks can be overcome in a particularly simple way with an inventive pants-type diaper, simply by using bands that are comprised of two parts which are joined together by means of a releasable and refastenable fastener means. FIGS. 7 and 8 are respective cross-sectional and side views of two such bands 33 and 34, while FIG. 9 illustrates a pants-type diaper provided with a band 33. The band 33 is comprised of two parts 35, 36 which are mutually joined by a row of projections 37 projecting from the part 35 and passing through a row of openings formed in the part 36. This enables the pants-type diaper illustrated in FIG. 9 to be removed and replaced without needing to fully remove trousers, pants or like garment worn outside the pant diaper, by loosening the band parts 35, 36 from one another so that either the rear part or the front part can be passed between the legs of the wearer. A replacement pants-type diaper can thereafter be put on by loosening the band parts of said pants-type diaper from each other, whereafter the front or rear part of the replacement pants-type diaper is inserted between the legs of the wearer. The two band parts are then fastened together, by inserting the row of projections on one band part through the row of openings in the other part, whereafter the pants-type diaper is drawn up to its correct wearing position in the same way as a pair of underpants, unless this has already been done when refastening the replacement pant diaper.

FIG. 8 illustrates schematically a band 34 which is comprised of two parts 38, 39 which are mutually joined by means of a mechanical fastener means 40, for instance a self-fastening or hook and loop band. The fastening means illustrated in FIGS. 7-9 merely represent examples of suitable fastener devices and it will be understood that the pants-type diaper shown in FIG. 9 can be provided with a number of other types of fasteners lying within the expertise of a normal person skilled in this art. For instance, adhesive fasteners can be used, and also other types of mechanical fasteners other than those described, such as buttons and buttonholes, hooks and eyes, etc.

Although the invention has been described and illustrated solely with reference to pants-type diapers, it will be understood that the invention can also be applied to sanitary panties, i.e. panties in which absorbent bodies for absorbing menstrual fluids or light incontinence discharges are integrated.

It will be understood that the described embodiments can be modified within the scope of the invention. For instance, the absorbent body may have a form different to that described and may include several layers, which in turn means that the described plant for manufacturing pants-type diapers in accordance with the invention will be modified correspondingly. Furthermore, the pants-type diaper blanks can be folded and the front and rear side parts of the blanks brought together with the aid of means other than those described. The individual pants-type diapers can be cut from the continuous web of blanks in conjunction with bringing the front and the rear side parts of the blanks together, instead of in a separate following stage. Furthermore, more than one band can be used to fasten the mutually opposing front and rear side parts. The invention is therefore restricted solely by the scope of the following claims.

We claim:

1. A method of manufacturing a pants-type diaper or a sanitary panty, starting from a flat blank which includes an elongated absorbent body enclosed between two casing sheets which at opposing front and rear end parts of the absorbent body have side parts which extend laterally beyond the body on both sides thereof, said method comprising the step of folding the blank around a transverse axis so that the end edges of the side parts lie edge-to-edge, characterized by placing at least one folded band of flexible material between each pair of front and rear side parts which oppose one another in the folded state of the blank, so that the free ends of the bands situated between the pairs of opposing side parts are turned against each other, and by fastening the free ends of said bands to adjacent side parts to form the pant-type diaper or sanitary panty.

[2. The method according to claim 1, further comprising placing the folded bands and fastening said bands to the front or the rear side parts prior to folding the blank.]

3. A method of manufacturing a pants-type diaper or a sanitary panty, starting from a flat blank which comprises an elongated absorbent body enclosed between two casing sheets which at opposing front and rear end parts of the absorbent body have side parts which extend laterally beyond the body and on opposite sides thereof, *wherein one of the casing sheets comprises a liquid-permeable inner layer and the other of the casing sheets comprises a liquid-impermeable outer layer,* wherein the blank is folded about a transverse axis so that the end edges of the side parts lie edge-to-edge, characterized by folding at least one band of flexible material about each pair of front and rear side parts which oppose one another in the folded state of the blank, and by fastening the free ends of the *folded* bands *directly* to *a surface of the* adjacent side parts *on the liquid-permeable inner layer which faces the wearer and is adapted to directly contact the wearer during use* to form the pants-type diaper or sanitary panty.

[4. The method according to claim 1, further comprising folding the bands in a bellows-like fashion prior to their attachment to the side parts.]

5. A pants-type diaper or sanitary panty, comprising:

an elongated absorbent body enclosed between two casing sheets which at opposing front and rear end parts of the absorbent body have side parts which extend laterally beyond *all portions of* said body on both sides thereof, *one casing sheet and the side parts thereof having the same lateral dimensions as the other casing sheet and the side parts thereof, and a lateral distance across longitudinal edges of the side parts on the front end part being the same as a lateral distance across longitudinal edges of the side parts on the rear end part,*

*the* opposing front and rear side parts are joined together during manufacture to form a circumferential waist opening and two predefined leg openings of the pants-type diaper or sanitary panty, wherein a separate piece of material, *that is* separate from the front and rear side parts *by not being integral with the front and rear side parts,* extends between each [pari] *pair* of *the* opposing front and rear side [pars] *parts* and forms a joint between these side parts such that said joint lies in a plane which is the same plane as the opposing front and rear side parts *so that surfaces of the front and rear side parts which face a wearer during use of the assembly are directly attached to a same side of the separate piece of material* and *the joint* will be subjected essentially to shear forces when the article is worn, *and the separate piece of material is formed of only non-elastic material.*

[6. The pants-type diaper or sanitary panty according to claim 5, wherein the pieces of material joining the side parts are essentially non-elastic.]

[7. The pants-type diaper or sanitary panty according to claim 5, wherein the separate pieces of material are joined to the inner surfaces of the side parts.]

[8. The pants-type diaper or sanitary panty according to claim 5, wherein the separate pieces of material are joined to the outer surfaces of the side parts.]

[9. The pants-type diaper or sanitary panty according to claim 5, wherein each separate piece of material is joined to the inner surface of one of the front or rear side parts and to the outer surface of the other front or rear side part.]

10. The pants-type diaper or sanitary panty according to claim 5, wherein the separate pieces of material are comprised of two separate parts which are mutually joined together by a releasable and refastenable fastener means.

11. The pants-type diaper or sanitary panty according to claim 10, wherein the fastener means comprises a row of press studs.

12. The pants-type diaper or sanitary panty according to claim 10, wherein the fastener means is comprised of projections which project from one of the separate parts of said piece and which pass through openings in the other of the separate parts of said piece.

13. The pants-type diaper or sanitary panty according to claim 10, wherein the fastener means is comprised of mutually coacting hooks and eyes.

14. The pants-type diaper or sanitary panty according to claim 10, wherein the fastener means is comprised of adhesive coatings.

15. The pants-type diaper or sanitary panty according to claim 10, wherein the fastener means is comprised of a self-fastening or hook and loop band.

16. The method according to claim 1, wherein said method comprises a method for continuous manufacturing of absorbent articles in the form of pants-type diapers or sanitary panties.

17. The pants-type diaper or sanitary panty according to claim 5, wherein the pieces of material include bands placed between each pair of front and rear side parts so that end edges of the side parts lie edge-to-edge.

*18. A pants-type diaper or sanitary panty, comprising:*

*an elongated absorbent body enclosed between two casing sheets, the casing sheets having an area of reduced lateral width at a central portion along the length of the casing sheets to form leg openings, and at opposing front and rear end parts of the absorbent body, the casing sheets have side parts which extend laterally beyond said body and the leg openings on both sides thereof, the side parts having lateral edges extending parallel to a longitudinal axis of the casing sheets, one casing sheet and the side parts thereof having the same lateral dimensions as the other casing sheet and the side parts thereof, and a lateral distance across longitudinal edges of the side parts on the front end part being the same as a lateral distance across longitudinal edges of the side parts on rear end part;*

*the opposing front and rear side parts are joined together during manufacture to form a circumferential waist opening and two predefined leg openings of the pants-type diaper or sanitary panty,*

*wherein only a single separate piece of material, separate from the front and rear side parts, extends between each pair of the opposing front and rear side parts and is directly connected to the side parts to form a joint between the side parts such that said joint lies in a plane which is the same plane as the opposing front and rear side parts so that said joint lies in a plane which is adjacent to and parallel with the opposing front and rear side parts and the joint will be subjected essentially to shear forces when the article is worn,*

*wherein each of the pairs of the opposing front and rear side parts are joined together by the respective single separate piece of material and the front and rear side parts are spaced apart by a predetermined distance such that the front and rear side parts do not overlap one another in the circumferential direction.*

*19. A pants-type diaper or sanitary panty, comprising:*

*an elongated absorbent body enclosed between two casing sheets which at opposing front and rear end parts of the absorbent body have side parts which extend laterally beyond said body on both sides thereof, both casing sheets having a longitudinal length and a lateral width, the lateral width being the greatest at each longitudinal end of the casing sheets;*

*the opposing front and rear side parts are joined together during manufacture to form a circumferential waist opening and two predefined leg openings of the pants-type diaper or sanitary panty,*

*wherein only a single separate piece of material, separate from the front and rear side parts, extends between each pair of the opposing front and rear side parts and is directly connected to the side parts to form a joint between the side parts such that said joint lies in a plane which is the same plane as the opposing front and rear side parts so that outside surfaces of the front and rear side parts are attached directly to a same side of the separate piece of material and the joint will be subjected essentially to shear forces when the article is worn,*

*wherein each of the pairs of the opposing front and rear side parts are joined together by the respective single separate piece of material and the front and rear side parts are not directly joined to one another and do not overlap one another when the article is worn, and the single separate piece of material is formed of only non-elastic material so that the material extending between each pair of the opposing front and rear side parts is non-elastic.*

*20. A pants-type diaper or sanitary panty, comprising:*

*an elongated absorbent body enclosed between two casing sheets which at opposing front and rear end parts of the absorbent body have side parts which extend laterally beyond said body on both sides thereof, one casing sheet and the side parts thereof having the same lateral dimensions as the other casing sheet and the side parts thereof, and a lateral distance across longitudinal edges of the side parts on the front end part being the same as a lateral distance across longitudinal edges of the side parts on rear end part,*

*the opposing front and rear side parts are joined together during manufacture to form a circumferential waist opening and two predefined leg openings of the pants-type diaper or sanitary panty, wherein only a separate piece of material, that is separate from the front and rear side parts by not being integral with the front and rear side parts, extends between each pair of the opposing front and rear side parts and forms a joint between these side parts such that said joint lies in a plane which is the same plane as the opposing front and rear side parts so that the front and rear side parts are directly attached to*

*a same side of the separate piece of material and the joint will be subjected essentially to shear forces when the article is worn, and the separate piece of material is folded when the opposing front and rear side parts lie parallel to each other;*

*the front and rear side parts are spaced from each other to thereby define a predetermined distance between the front and rear side parts as measured along a circumferential direction of the circumferential waist; and*

*the separate piece of material is formed of only non-elastic material and the separate piece of material is non-elastic so that the predetermined distance remains constant when the pants-type diaper or sanitary panty is worn.*

*21. A pants-type diaper or sanitary panty, comprising:*

*an elongated absorbent body enclosed between two casing sheets which at opposing front and rear end parts of the absorbent body have side parts which extend laterally beyond said body on both sides thereof,*

*the opposing front and rear side parts are joined together during manufacture to form a circumferential waist opening and two predefined leg openings of the pants-type diaper or sanitary panty, wherein only a separate piece of material, that is separate from the front and rear side parts by not being integral with the front and rear side parts and which extends between each pair of the opposing front and rear side parts and forms a joint between these side parts, such that the side parts are not directly joined to each other and do not overlap one another when the article is worn, and such that said joint lies in a plane which is the same plane as the opposing front and rear side parts so that outside surfaces of the front and rear side parts are directly attached to a same side of the separate piece of material and the joint will be subjected essentially to shear forces when the article is worn, and the separate piece of material is formed of only non-elastic material so that the material extending between each pair of the opposing front and rear side parts is non-elastic.*

*22. A pants-type diaper or sanitary panty, comprising:*

*an elongated absorbent body enclosed between two casing sheets which at opposing front and rear end parts of the absorbent body have side parts which extend laterally beyond said body on both sides thereof, one casing sheet and the side parts thereof having the same lateral dimensions as the other casing sheet and the side parts thereof, and a lateral distance across longitudinal edges of the side parts on the front end part being the same as a lateral distance across longitudinal edges of the side parts on rear end part,*

*the opposing front and rear side parts are joined together during manufacture to form a circumferential waist opening and two predefined leg openings of the pants-type diaper or sanitary panty, wherein only a separate piece of material, that is separate from the front and rear side parts by not being integral with the front and rear side parts and which extends between each pair of the opposing front and rear side parts and forms a joint between these side parts such that said joint lies in a plane which is the same plane as the opposing front and rear side parts so that the front and rear side parts are directly attached to a same side of the separate piece of material and the joint will be subjected essentially to shear forces and the front and rear side parts are non-overlapping in the circumferential direction when the article is worn, the separate piece of material made up of only non-elastic material so that the material extending between each pair of the opposing front and rear side parts is non-elastic.*

*23. A pants-type diaper or sanitary panty, comprising:*

*an elongated absorbent body enclosed between two casing sheets which at opposing front and rear end parts of the absorbent body have side parts which extend laterally beyond all portions of said body on both sides thereof, one casing sheet and the side parts thereof having the same lateral dimensions as the other casing sheet and the side parts thereof, and a lateral distance between longitudinal edges of the side parts on the front end part being the same as a lateral distance between longitudinal edges of the side parts on rear end part,*

*the opposing front and rear side parts are joined together during manufacture to form a circumferential waist opening and two predefined leg openings of the pants-type diaper or sanitary panty, wherein a separate piece of material, that is separate from the front and rear side parts by not being integral with the front and rear side parts extends between each pair of the opposing front and rear side parts and a joint is formed between each of these side parts such that said joint lies in a plane which is the same plane as the opposing front and rear side parts so that the front and rear side parts are directly attached to a side of the separate piece of material that faces away from a wearer during use and the joint will be subjected essentially to shear forces when the article is worn, wherein the joint is a mechanical joint of a self-fastening type.*

*24. A pants-type diaper or sanitary panty, comprising:*

*an elongated absorbent body enclosed between two casing sheets which at opposing front and rear end parts of the absorbent body have side parts which extend laterally beyond said body on both sides thereof, one casing sheet and the side parts thereof having the same lateral dimensions as the other casing sheet and the side parts thereof, and both casing sheets having a longitudinal length and a lateral width, the lateral width being the greatest at each longitudinal end of the casing sheets;*

*the opposing front and rear side parts are joined together during manufacture to form a circumferential waist opening and two predefined leg openings of the pants-type diaper or sanitary panty, wherein a separate piece of material, that is separate from the front and rear side parts by not being integral with the front and rear side parts, extends between each pair of the opposing front and rear side parts and forms a joint between these side parts such that said joint lies in a plane which is the same plane as the opposing front and rear side parts so that the front and rear side parts are directly attached to a same side of the separate piece of material, the joint will be subjected essentially to shear forces when the article is worn and the front and rear side parts are spaced from each other to thereby define a predetermined distance between the front and rear side parts as measured along a circumferential direction of the circumferential waist, the separate piece of material is formed of only non-elastic material so that the material extending between each pair of the opposing front and rear side parts is non-elastic.*

*25. A pants-type diaper or sanitary panty according to claim 24, wherein outside surfaces of the front and rear side parts are attached to a same side of the separate piece of material.*

*26. A pants-type diaper or sanitary panty according to claim 24, wherein inside surfaces of the front and rear side parts are attached to a same side of the separate piece of material.*

*27. A pants-type diaper or sanitary panty, comprising:*

*an elongated absorbent body enclosed between two casing sheets which at opposing front and rear end parts of the absorbent body have side parts which extend laterally beyond said body on both sides thereof, one casing sheet and the side parts thereof having the same lateral dimensions as the other casing sheet and the side parts thereof,*

*the opposing front and rear side parts are joined together during manufacture to form a circumferential waist opening and two predefined leg openings of the pants-type diaper or sanitary panty,*

*wherein a separate piece of material, that is separate from the front and rear side parts by not being integral with the front and rear side parts, extends between each pair of the opposing front and rear side parts and forms a joint between the side parts such that said joint lies in a plane which is the same plane as the opposing front and rear side parts,*

*wherein said separate piece of material lies in said plane such that the front and rear side parts are directly attached to a same side of the separate piece of material and the joint will be subjected essentially to shear forces when the article is worn, and*

*wherein the separate piece of material joining the front and rear side parts includes two parts formed of the same material, each part of the two parts having two ends, a first end of one part is positioned adjacent to a first end of the other part, and the first ends joined to each other by a mechanical fastener of a self-fastening type, and second opposite ends of each part are joined to a respective front or rear side part.*

*28. A pants-type diaper or sanitary panty, comprising:*

*an elongated absorbent body enclosed between two casing sheets which at opposing front and rear end parts of the absorbent body have side parts which extend laterally beyond all portions of said body on both sides thereof, one casing sheet and the side parts thereof having the same lateral dimensions as the other casing sheet and the side parts thereof, and a lateral distance across longitudinal edges of the side parts on the front end part being the same as a lateral distance across longitudinal edges of the side parts on rear end part,*

*the opposing front and rear side parts are joined together during manufacture to form a circumferential waist opening and two predefined leg openings of the pants-type diaper or sanitary panty,*

*wherein a separate piece of material, that is separate from the front and rear side parts by not being integral with the front and rear side parts, extends between each pair of the opposing front and rear side parts and forms a joint between these side parts such that said joint lies in a plane which is the same plane as the opposing front and rear side parts so that surfaces of the front and rear side parts which face a wearer during use of the assembly are directly attached to a same side of the separate piece of material and the joint will be subjected essentially to shear forces when the article is worn, and*

*wherein the separate pieces of material are each comprised of two separate parts which are mutually joined together by a releasable and refastenable fastener means.*

* * * * *